US008591542B2

United States Patent
White et al.

(10) Patent No.: US 8,591,542 B2
(45) Date of Patent: *Nov. 26, 2013

(54) TISSUE PUNCTURE CLOSURE METHOD WITH DISENGAGABLE AUTOMATIC TAMPING SYSTEM

(75) Inventors: John O. White, Lakeville, MN (US); Russell D. Terwey, St. Michael, MN (US)

(73) Assignee: St. Jude Medical Puerto Rico LLC, Caguas, PR (US)

( * ) Notice: Subject to any disclaimer, the term of this patent is extended or adjusted under 35 U.S.C. 154(b) by 766 days.

This patent is subject to a terminal disclaimer.

(21) Appl. No.: 12/574,481

(22) Filed: Oct. 6, 2009

(65) Prior Publication Data

US 2010/0023051 A1    Jan. 28, 2010

Related U.S. Application Data

(62) Division of application No. 11/130,688, filed on May 17, 2005, now Pat. No. 7,618,438.

(51) Int. Cl.
*A61B 17/08* (2006.01)

(52) U.S. Cl.
USPC .......................................... 606/213; 606/232

(58) Field of Classification Search
USPC ................. 606/139, 142, 144–148, 213, 232; 74/113; 475/125
See application file for complete search history.

(56) References Cited

U.S. PATENT DOCUMENTS

| | | | |
|---|---|---|---|
| 4,744,364 A | 5/1988 | Kensey | |
| 4,890,612 A | 1/1990 | Kensey | |
| 5,021,059 A | 6/1991 | Kensey et al. | |
| 5,222,974 A | 6/1993 | Kensey et al. | |
| 5,282,827 A | 2/1994 | Kensey et al. | |
| 5,290,310 A | 3/1994 | Makower et al. | |
| 5,411,520 A | 5/1995 | Nash et al. | |
| 5,531,759 A | 7/1996 | Kensey et al. | |
| 5,662,681 A | 9/1997 | Nash et al. | |
| 5,707,393 A | 1/1998 | Kensey et al. | |
| 5,935,147 A | 8/1999 | Kensey et al. | |
| 6,162,192 A | 12/2000 | Cragg et al. | |
| 6,682,489 B2 | 1/2004 | Tenerz et al. | |
| 6,860,895 B1 | 3/2005 | Akerfeldt et al. | |
| 7,931,670 B2 * | 4/2011 | Fiehler et al. | 606/213 |
| 2005/0085851 A1 | 4/2005 | Fiehler et al. | |

* cited by examiner

*Primary Examiner* — Gregory Anderson
(74) *Attorney, Agent, or Firm* — Holland & Hart (57) ABSTRACT

A method and apparatus for sealing a puncture or incision formed percutaneously in tissue separating two internal portions of the body of a living being with an anchor, a sealing plug and a filament connecting the anchor and sealing plug. The method and apparatus provide for disengagable automatic tamping and/or cinching of the sealing plug when the apparatus is withdrawn from the puncture site. The disengagable automatic tamping and/or cinching is facilitated by transducing a motive force generated by the withdrawal of the apparatus into a tamping and/or cinching force.

16 Claims, 10 Drawing Sheets

TISSUE PUNCTURE CLOSURE METHOD WITH DISENGAGABLE AUTOMATIC TAMPING SYSTEM

RELATED APPLICATION

This is a divisional of U.S. patent application Ser. No. 11/130,688 now U.S. Pat. No. 7,618,438, filed on 17 May 2005, the disclosure of which is incorporated, in its entirety, by this reference.

FIELD OF THE INVENTION

This invention relates generally to medical devices and more particularly to devices for sealing punctures or incisions in a tissue wall.

BACKGROUND

Various surgical procedures are routinely carried out intravascularly or intraluminally. For example, in the treatment of vascular disease, such as arteriosclerosis, it is a common practice to invade the artery and insert an instrument (e.g., a balloon or other type of catheter) to carry out a procedure within the artery. Such procedures usually involve the percutaneous puncture of the artery so that an insertion sheath can be placed in the artery and thereafter instruments (e.g., catheter) can pass through the sheath and to an operative position within the artery. Intravascular and intraluminal procedures unavoidably present the problem of stopping the bleeding at the percutaneous puncture after the procedure has been completed and after the instruments (and any insertion sheaths used therewith) have arterial punctures, is typically stopped by utilizing vascular closure devices, such as those described in U.S. Pat. Nos. 6,179,963; 6,090,130; and 6,045,569 and related patents that are hereby incorporated by reference.

Typical closure devices such as the ones described in the above-mentioned patents place a sealing plug at the tissue puncture site. Successful deployment of the sealing plug, however, requires that it be manually ejected from within a device sheath and tamped down to an outer surface of the tissue puncture using a tamping tube. The tamping procedure cannot commence until the device sheath (within which the tamping tube is located) has been removed so as to expose the tamping tube for manual grasping. Under certain conditions, removal of the sheath prior to tamping the sealing plug may cause the sealing plug itself to be displaced proximally from the tissue puncture, hindering subsequent placement of the sealing plug, and resulting in only a partial seal and associated late bleeding from the tissue puncture. Accordingly, there is a need for improving the mechanism for deployment of the sealing plug at the site of a tissue puncture.

SUMMARY

The present invention meets the above-described needs and others. Specifically, the present invention provides methods and systems for closing internal tissue punctures. However, unlike prior systems, the present invention provides automatic tamping to a sealing plug as the closure device is retracted. In addition, the present invention allows the automatic tamping system to disengage, facilitating full retraction of the closure device and easy separation of the sealing plug from the remainder of the closure device.

In one of many possible embodiments, the present invention provides a tissue puncture closure device for partial insertion into and sealing of an internal tissue wall puncture. The closure device includes a filament extending from a first end of the closure device to a second end of the closure device, an anchor for insertion through the tissue wall puncture attached to the filament at the second end of the closure device, a sealing plug slidingly attached to the filament adjacent to the anchor, and a selectably disengagable automatic driving mechanism for automatically tamping or cinching the sealing plug toward the second end upon withdrawal of the closure device from the internal tissue wall puncture. The device may include a tamping tube disposed adjacent to the sealing plug, such that the tamping tube is driven by the automatic driving mechanism to tamp the sealing plug.

According to some embodiments, the automatic driving mechanism includes a transducer for effecting a tamping force on the sealing plug upon withdrawal of the closure device from the tissue wall puncture. The transducer may include a first gear and spool assembly with a portion of the filament wound thereon, and a tamping tube driver directly or indirectly driven by the first gear. The tamping tube driver may comprise a rack slidingly disposed about the filament. As the spool rotates in response to retraction of the closure device, it drives the first gear in a first direction, and the first gear drives the tamping tube driver directly or indirectly in a second direction. The tamping tube driver or rack may also comprise the tamping tube.

According to some embodiments, the gear may in fact be a gear train with a gear ratio of at least of 2.5:1 with respect to the spool. A torque-limiting and/or manually operable clutch may be disposed between the spool and the gear according to some embodiments. The gear train is capable of transducing a retraction force in a first direction into a distal force on the sealing plug in a second direction upon withdrawal of the closure device from the tissue wall puncture. The gear train may comprise the first gear and spool assembly on a first axis with a portion of the filament wound thereon, a second gear on a second axis adjacent to the first gear, and a third gear on a third axis adjacent to the second gear. At least one of the first, second, or third gears may be movable along its respective axis to operatively connect and disconnect the first, second, and third gears. The clutch may selectively connect and disconnect the spool from the first gear.

According to some embodiments there may be a biasing member on the second axis biasing the second gear into a meshed relationship with the first and third gears and an actuator coupled to the second gear for selectively overcoming the biasing member to move the second gear axially out of the meshed relationship with at least one of the first and third gears. According to some embodiments there is a rack meshed with the third gear, such that the rack also interlocks with the second gear and locks out the actuator in a first rack position. The rack allows the actuator to move when the rack is in a second rack position. The first rack position may comprise an initial position and the second rack position may comprise a deployed plug position. The tamping tube may be disposed between the rack and the sealing plug.

Another aspect of the invention provides a tissue puncture closure device for partial insertion into and sealing of a tissue puncture in an internal tissue wall accessible through a percutaneous incision, comprising an anchor for disposition on a distal side of the internal tissue wall a sealing plug for disposition on a proximal side of the internal tissue wall, and a filament connected to and anchored at a distal end to the anchor and sealing plug for slidably cinching the anchor and sealing plug together about the tissue puncture. The sealing plug is slidably disposed on the filament proximal to the anchor and a tamping device is disposed on the filament for driving the sealing plug along the filament distally towards the anchor. A proximal end of the filament is wound on storage spool, which may share a common first axis of rotation with a first gear. The device may include a second gear having a second axis of rotation, the second gear selectively movable along the second axis of rotation into engagement and disengagement with the first gear for providing a tamping force to the tamping device. The embodiment may further comprise a third gear engaged with the second gear and a rack.

According to some embodiments, there is an actuator coupled to the second gear, and a spring biasing the second gear to a first position. Applying a force to the actuator sufficient to overcome the spring moves the second gear along the second axis of rotation to a second position. However, there may be an interlocking geometry between the rack and the second gear wherein the interlocking geometry prevents movement of the second gear in at least one axial direction along the second axis of rotation with the rack in a first rack position, but allows movement of the second gear in the at least one axial direction with the rack in a second rack position. Accordingly, there may be a second gear hub with an annular groove disposed therein such that the rack is at least partially disposed in the annular groove in a first rack position. The rack moves out of the annular groove to a second rack position in response to rotation of the third gear.

Another aspect of the invention provides a method of sealing a tissue puncture in an internal tissue wall accessible through a percutaneous incision. The method includes withdrawing a closure device from the tissue puncture, automatically transducing a motive force generated by withdrawal of the closure device in a first direction to a cinching or tamping force in a second direction, and manually disabling the tamping force in the second direction. The method may comprise applying the cinching or tamping force in the second direction to a sealing plug. The motive force may be transferred to a rack that is slidingly disposed about a filament, the filament being connected to the sealing plug. The transferring may include automatically unwinding the filament from a spool by deploying an anchor attached to the filament inside the tissue puncture, and withdrawing the closure device from the tissue puncture. The transferring may further comprises driving a gear train meshed with the rack and connected to the spool via the unwinding of the spool. Manually disabling the tamping force in the second direction may comprise disengaging at least one gear of the gear train, for example by axially displacing at least one gear out of contact with an adjacent gear.

Another aspect of the invention provides a method of sealing a tissue puncture in an internal tissue wall accessible through a percutaneous incision. The method comprises providing a tissue puncture closure device comprising a filament connected at its distal end to an anchor and to a sealing plug located proximal of the anchor for disposition and anchoring about the tissue puncture, the tissue puncture closure device also comprising an automatic tamping device, inserting the tissue puncture closure device into the percutaneous incision, deploying the anchor into the tissue puncture, at least partially withdrawing the closure device from the percutaneous incision, automatically tamping the sealing plug toward the anchor upon withdrawal of the closure device from the internal tissue wall puncture with the automatic tamping device, disengaging the automatic tamping device, retracting the tissue puncture closure device, exposing the filament, cutting the filament, and leaving the anchor and the sealing plug at the tissue puncture.

Additional advantages and novel features of the invention will be set forth in the description which follows or may be learned by those skilled in the art through reading these materials or practicing the invention. The advantages of the invention may be achieved through the means recited in the attached claims.

BRIEF DESCRIPTION OF THE DRAWINGS

The accompanying drawings illustrate various embodiments of the present invention and are a part of the specification. The illustrated embodiments are merely examples of the present invention and do not limit the scope of the invention.

Throughout the drawings, identical reference numbers designate similar, but not necessarily identical, elements.

DETAILED DESCRIPTION

As mentioned above, vascular procedures are conducted throughout the world and require access to an artery through a puncture. Most often, the artery is a femoral artery. To close the puncture following completion of the procedure, many times a closure device is used to sandwich the puncture between an anchor and a sealing plug. However, sometimes the sealing plug is difficult to eject from the sealing device and may not properly seat against an exterior situs of the arteriotomy. If the plug does not seat properly against the arteriotomy, there is a potential for elongated bleeding. The present invention describes methods and apparatus that facilitate sealing plug ejection and proper placement of the sealing plug. While the vascular instruments shown and described below include procedure sheaths and puncture sealing devices, the application of principles described herein are not limited to the specific devices shown. The principles described herein may be used with any medical device. Therefore, while the description below is directed primarily to arterial procedures and certain embodiments of a vascular closure device, the methods and apparatus are only limited by the appended claims.

As used in this specification and the appended claims, the term "tamp" or "tamping" is used broadly to mean packing down by one or a succession of blows or taps or smooth, steady pressure, but not by excessive force. "Engage" and "engabable" are also used broadly to mean interlock, mesh, or contact between two devices. Likewise "disengage" or "disengagable" means to remove or capable of being removed from interlock, mesh, or contact. A "spool" is a cylinder or other device on which something else is at least partially wound. A "tube" is an elongated device with a passageway. The passageway may be enclosed or open (e.g. a trough). A "lumen" refers to any open space or cavity in a bodily organ, especially in a blood vessel. "Slidingly mounted" means movable relative to an appropriate support. A "detent" is a catch or lever that locks, at least temporarily, the movement of one part of a mechanism. "Free floating" means able to move freely according to at least one degree of freedom, at least after overcoming any initial holder. "Free floating" movement is not necessarily unlimited, and may include free movement only within a specified range. "Transduce" means to convert a force or other input energy in one form into output energy or forces of another form or direction. The term "effecting" means producing an outcome, achieving a result, or bringing about. The words "including" and "having," as used in the specification, including the claims, have the same meaning as the word "comprising."

Referring now to the drawings, and in particular to FIGS. 1-4, a vascular puncture closure device 100 is shown according to the prior art. The vascular puncture closure device 100 includes a carrier tube 102 with a filament or suture 104 extending at least partially therethrough. The closure device 100 also includes a first or proximal end 106 and a second or distal end 107. External to a second or distal end 107 of the carrier tube 102 is an anchor 108. The anchor is an elongated, stiff, low profile member including an eye 109 formed at the middle. The anchor 108 is typically made of a biologically resorbable polymer.

The suture 104 is threaded through the anchor 108 and back to a collagen pad 110. The collagen pad 110 may be comprised of randomly oriented fibrous material bound together by chemical means. The collagen pad 110 is slidingly attached to the suture 104 as the suture passes distally through the carrier tube 102, but as the suture traverses the anchor 108 and reenters the carrier tube 102, it is securely slip knotted proximal to the collagen pad 110 to facilitate cinching of the collagen pad 110 when the closure device 100 is properly placed and the anchor 108 deployed (see FIG. 4).

The carrier tube 102 typically includes a tamping tube 112 disposed therein. The tamping tube 112 is slidingly mounted on the suture 104 and may be used by an operator to tamp the collagen pad 110 toward the anchor 108 at an appropriate time to seal a percutaneous tissue puncture.

Prior to deployment of the anchor 108 within an artery, the eye 109 of the anchor 108 rests outside the distal end 107 of the carrier tube 102. The anchor 108 may be temporarily held in place flush with the carrier tube 102 by a bypass tube 114 disposed over the distal end 107 of the carrier tube 102.

Figure 1:
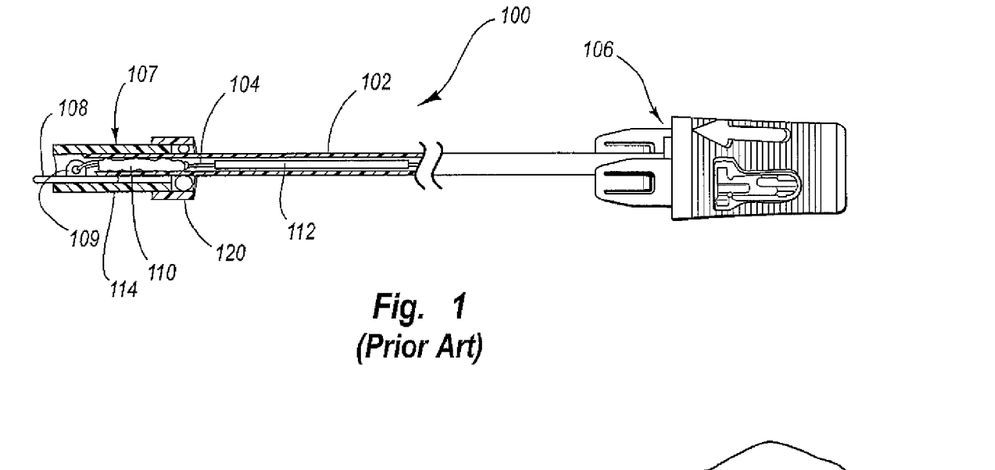
FIG. 1 is a partial cut-away view of a tissue closure device according to the prior art.
Figure 2:
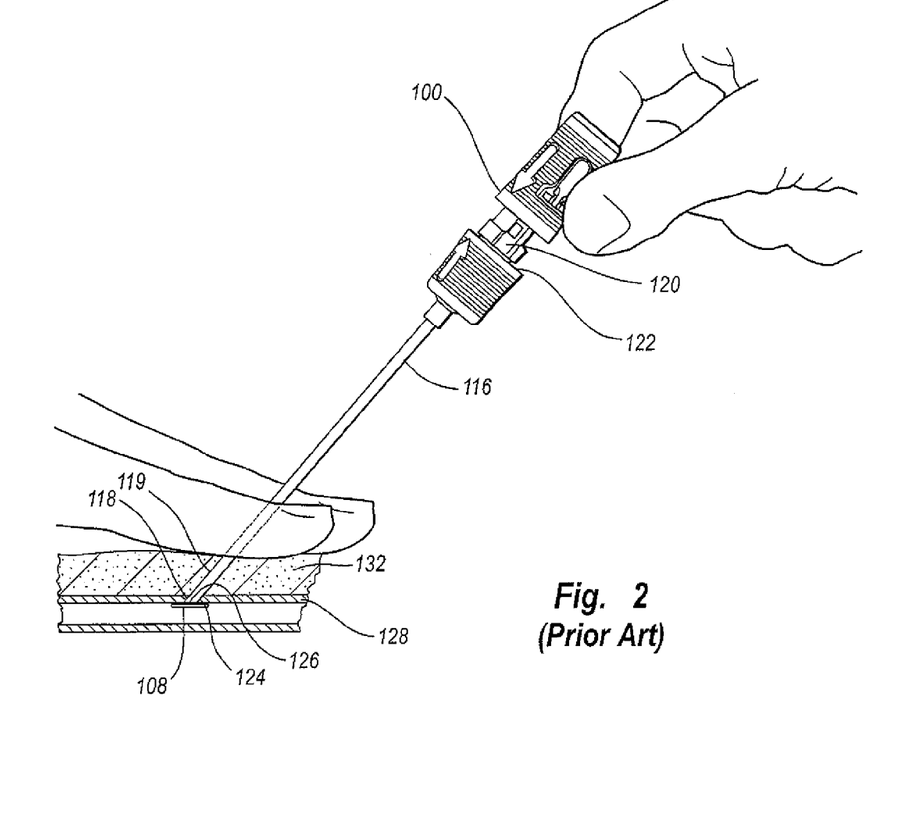
FIG. 2 is a side view of the tissue closure device of FIG. 1 engaged with an artery according to the prior art.
Figure 3:
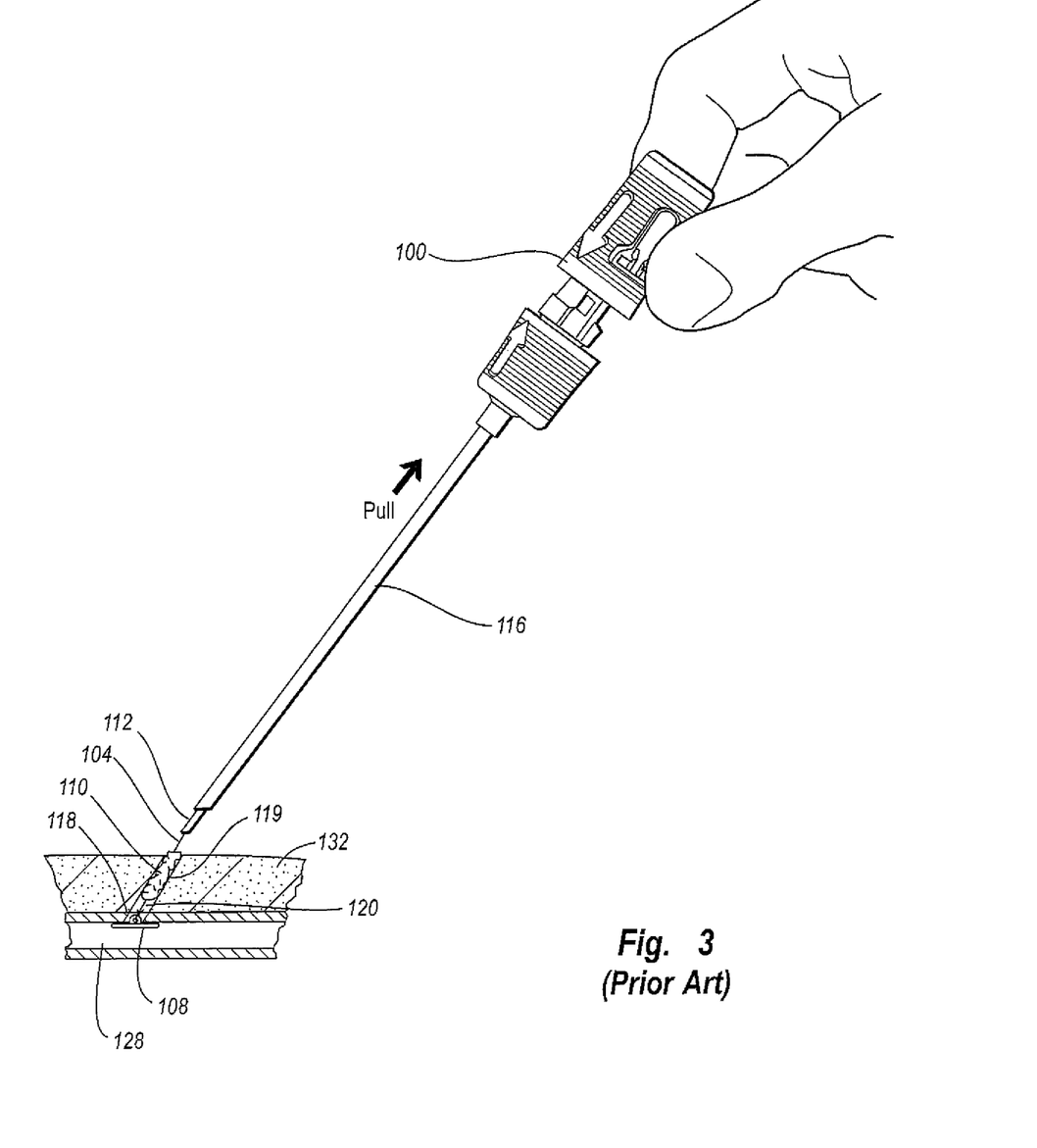
FIG. 3 is a side view of the tissue closure device of FIG. 1 being withdrawn from an artery according to the prior art to deploy a collagen sponge.
Figure 4:
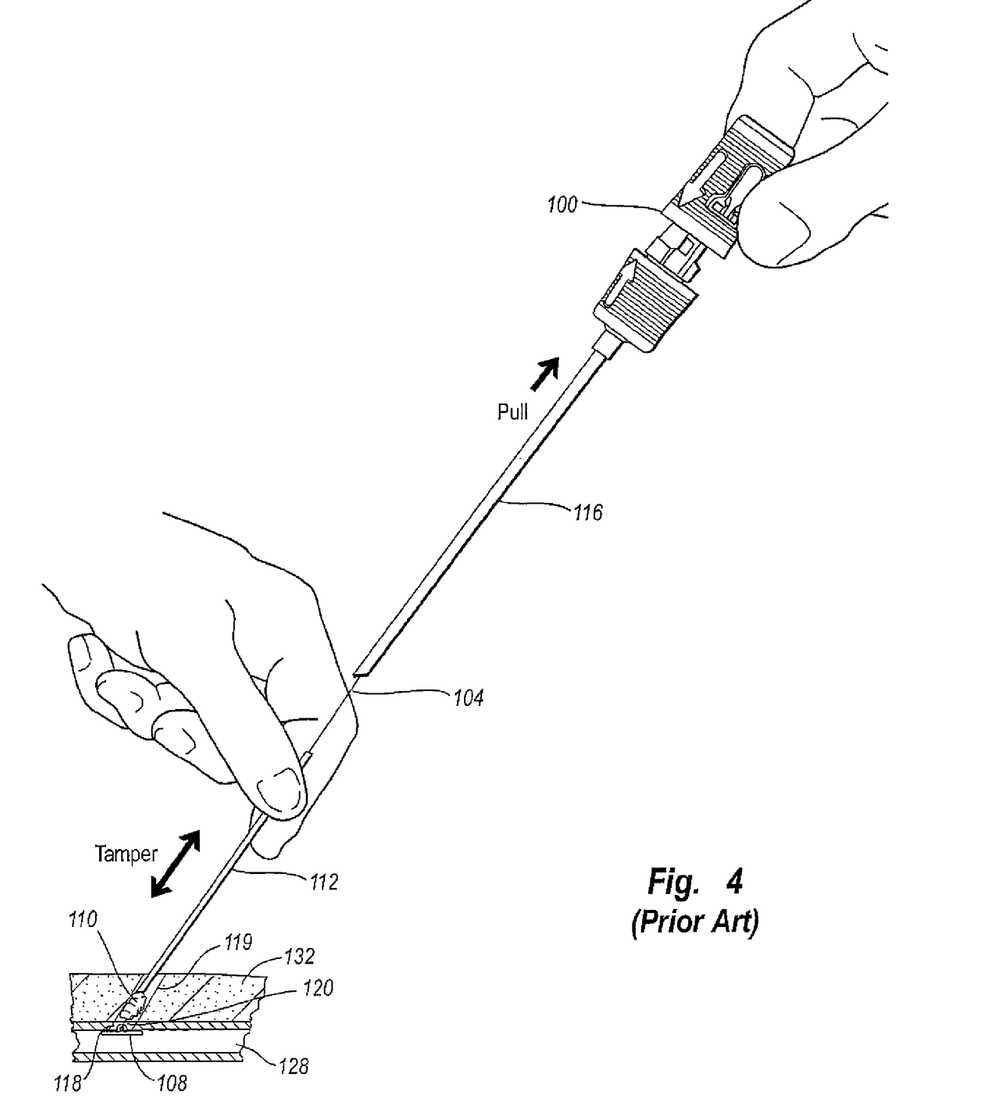
FIG. 4 is a side view of the tissue closure device of FIG. 1 illustrating tamping of the collagen sponge according to the prior art.

The flush arrangement of the anchor 108 and carrier tube 102 allows the anchor 108 to be inserted into a procedure sheath such as insertion sheath 116 as shown in FIGS. 2-4, and eventually through an arterial puncture 118. The insertion sheath 116 is shown in FIGS. 2-4 inserted through a percutaneous incision 119 and into an artery 128. However, the bypass tube 114 (FIG. 1) includes an oversized head 120 that prevents the bypass tube 114 from passing through an internal passage of the insertion sheath 116. Therefore, as the puncture closure device 100 is inserted into the insertion sheath 116, the oversized head 120 bears against a surface 122 of insertion sheath 116. Further insertion of the puncture closure device 100 results in sliding movement between the carrier tube 102 (FIG. 1) and the bypass tube 114, releasing the anchor 108 from the bypass tube 114 (FIG. 1). However, the anchor 108 remains in the flush arrangement shown in FIG. 1 following release from the bypass tube 114, limited in movement by the insertion sheath 116.

The insertion sheath 116 includes a monofold 124 at a second or distal end 126 thereof. The monofold 124 acts as a one-way valve to the anchor 108. The monofold 124 is a plastic deformation in a portion of the insertion sheath 116 that elastically flexes as the anchor 108 is pushed out through the distal end 126 of the insertion sheath 116. Typically, after the anchor 108 passes through the distal end 126 of the insertion sheath 116 and enters the artery 128, the anchor 108 is no longer constrained to the flush arrangement with respect to the carrier tube 102 and it deploys and rotates to the position shown in FIG. 2.

Referring next to FIGS. 3-4, with the anchor 108 deployed, the puncture closure device 100 and the insertion sheath 116 are withdrawn together, ejecting the collagen pad 110 from the carrier tube 102 into the incision tract 119 and exposing the tamping tube 112. With the tamping tube 112 fully exposed as shown in FIG. 4, the collagen pad 110 is manually tamped, and the anchor 108 and collagen pad 110 are cinched together and held in place with the self-tightening slip-knot on the suture 102. Thus, the tissue puncture is sandwiched between the anchor 108 and the collagen pad 110, thereby sealing the tissue puncture 118. The suture 104 is then cut and the incision tract 119 may be closed. The suture 104, anchor 108, and collagen pad 110 are generally made of resorbable materials and therefore remain in place while the puncture 118 heals.

Using the typical tissue puncture closure device 100 described above, however, it may be difficult to eject and tamp of the collagen pad 110. The insertion sheath 116 resists deformation as the collagen pad 110 is ejected from the carrier tube and tamping cannot commence until the sheath 116 has been removed so as to expose the tamping tube 112 for manual grasping. Under certain conditions, removal of the sheath 116 prior to tamping the collagen pad 110 causes the collagen pad 110 to retract or displace proximally from the tissue puncture 118, creating an undesirable gap 120 between the collagen pad 110 and the puncture 118. The gap 120 may remain even after tamping as shown in FIG. 4, and sometimes results in only a partial seal and bleeding from the tissue puncture 118.

Therefore, the present specification describes a medical device such as a tissue puncture closure device that is capable of retracting a procedural sheath relative to a closure device, exposing a distal end of the closure device prior to ejecting a sealing plug. The closure device also automatically drives the sealing plug toward a tissue puncture upon withdrawal of the tissue puncture closure device from the tissue puncture site. The mechanism for automatically driving the sealing plug may be selectably disengagable.

As described above, the general structure and function of tissue closure devices used for sealing a tissue puncture in an internal tissue wall accessible through an incision in the skin are well known in the art. Applications of closure devices including those implementing principles described herein include closure of a percutaneous puncture or incision in tissue separating two internal portions of a living body, such as punctures or incisions in blood vessels, ducts or lumens, gall bladders, livers, hearts, etc.

Referring now to FIGS. 5A-5G, a medical device, for example a tissue wall puncture closure device 200, is shown according to one embodiment of the present invention. The closure device 200 is shown in an assembly view in FIG. 5A. FIGS. 5B-5G illustrate the closure device 200 assembled and inserted through a procedure sheath 216 and into a lumen 232. The closure device 200 has particular utility when used in connection with intravascular procedures, such as angiographic dye injection, cardiac catheterization, balloon angioplasty and other types of recanalizing of atherosclerotic arteries, etc. as the closure device 200 is designed to cause immediate hemostasis of the blood vessel (e.g., arterial) puncture. However, it will be understood that while the description of the preferred embodiments below are directed to the sealing off of percutaneous punctures in arteries, such devices have much more wide-spread applications and can be used for sealing punctures or incisions in other types of tissue walls as well. Thus, the sealing of a percutaneous puncture in an artery, shown herein, is merely illustrative of one particular use of the closure device 200 of the present invention.

The closure device 200 includes a first or proximal end portion 206 and a second or distal end portion 207. A carrier tube 202 extends from the proximal end portion 206 to the distal end portion 207 and includes an outlet 213 at the distal end portion 207. The distal end portion 207 may include a slit 209.

Figure 5A:
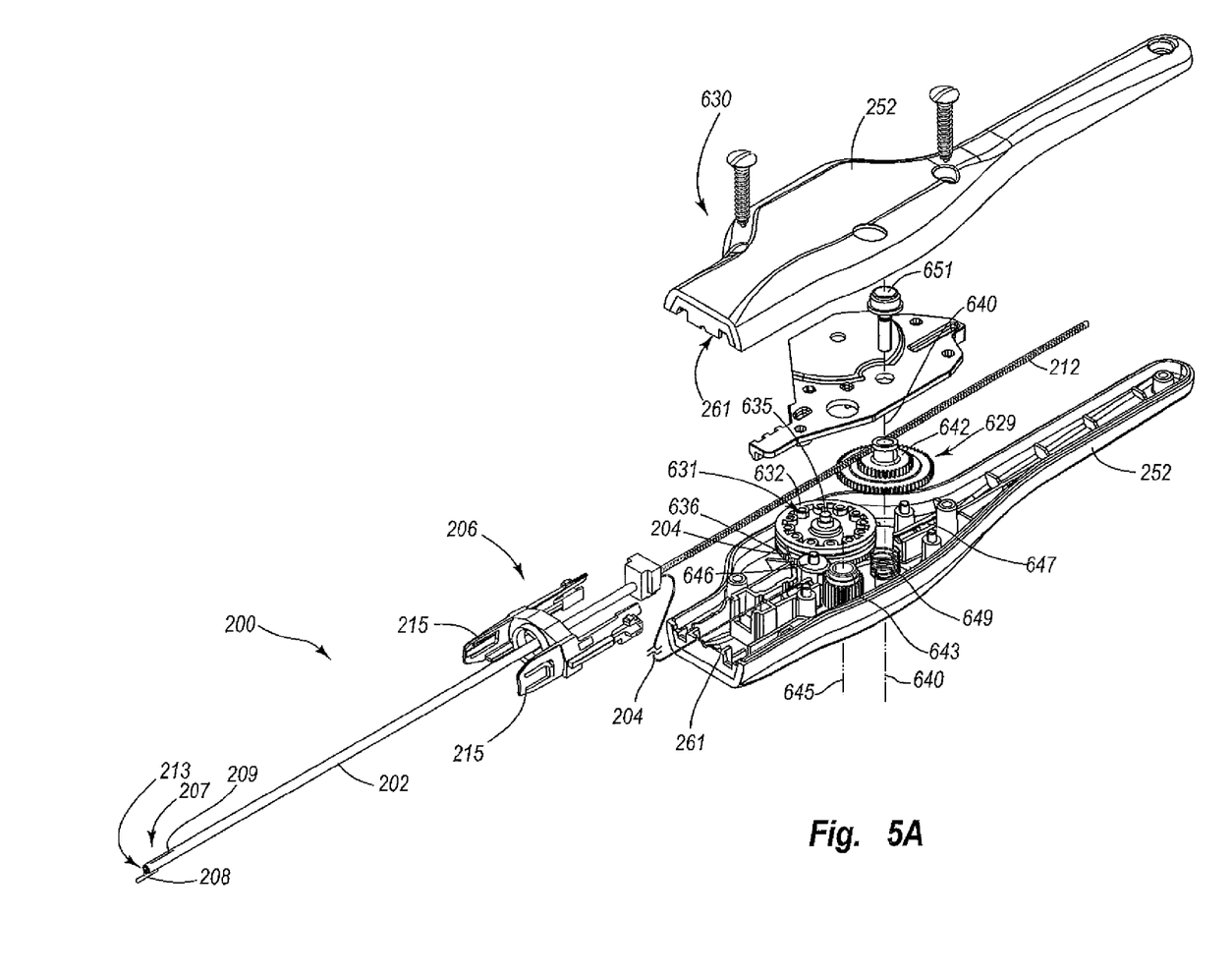
FIG. 5A is a perspective assembly view of a tissue puncture closure device with an automatic tamping or driving mechanism according to one embodiment of the present invention.
Figures 5B, 5C:
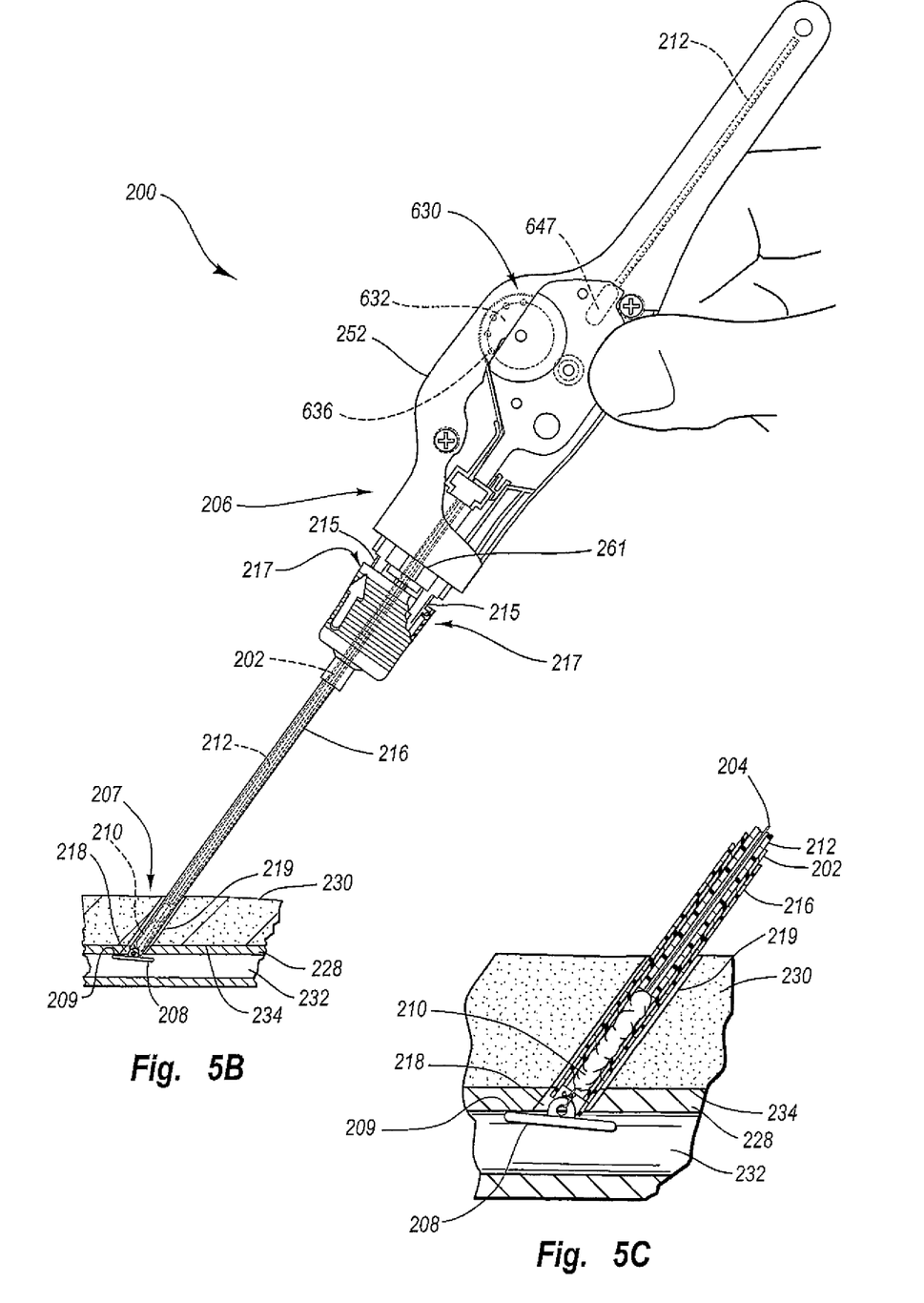
FIG. 5B is a side view of the tissue closure device of FIG. 5A inserted into a procedure sheath and shown engaged with an artery in a first position according to one embodiment of the present invention.
FIG. 5C is a detailed inset of FIG. 5B.

The carrier tube 202 may be made of plastic or other material and is designed for insertion through the procedure sheath 216 (FIG. 5B). The procedure sheath 216 (FIG. 5B) is designed for insertion through a percutaneous incision 219 (FIG. 5B) in a tissue layer 230 and into the lumen 232. According to FIGS. 5B-5G, the lumen 232 comprises an interior portion of a femoral artery 228.

At the distal end portion 207 of the carrier tube 202 there is an anchor 208 and a sealing plug 210 (FIG. 5B). The anchor 208 of the present embodiment is an elongated, stiff, low-profile member arranged to be seated inside the artery 228 (FIG. 5B) against an artery wall 234 (FIG. 5B) contiguous with a puncture 218 (FIG. 5B). The anchor 208 is preferably made of a biologically resorbable polymer. The sealing plug 210 (FIG. 5B) is formed of a compressible sponge, foam, or fibrous mat made of a non-hemostatic biologically resorbable material such as collagen, and may be configured in any shape so as to facilitate sealing the tissue puncture 218 (FIG. 5B).

The sealing plug 210 and anchor 208 are connected to one another by a filament or suture 204 that is also biologically resorbable. The anchor 208, the sealing plug 210, and the suture 204 are collectively referred to as the "closure elements" below. As shown in FIG. 5A, the anchor 208 is initially arranged adjacent to and exterior of the distal end portion 207 of the carrier tube 202, while the sealing plug 210 (FIG. 5B) is initially disposed within the carrier tube 202. The anchor 208 is shown nested in its low profile configuration along the carrier tube 202 to facilitate insertion into the lumen 232 in FIG. 5A, and deployed with a first surface 236 abutting the artery wall 234 in FIGS. 5B-5G. The suture 204 extends distally from the first end portion 206 of the closure device 200 through the carrier tube 202. The suture 204 may be threaded through one or more perforations in the sealing plug 210, through a hole in the anchor 208, and proximally back toward the carrier tube 202 to the sealing plug 210. The suture 204 is preferably threaded again through a perforation or series of perforations in the sealing plug 210. The suture 204 may also be threaded around itself to form a self-tightening slip-knot. The suture 204 may thus connect the anchor 208 and the sealing plug 210 in a pulley-like arrangement to cinch the anchor 208 and the sealing plug 210 together when the carrier tube 202 is pulled away from the anchor 208 and the sealing plug 210. The anchor 208 and the sealing plug 210 sandwich and lock the anchor and plug together, sealing the tissue puncture 218.

The carrier tube 202 houses a tamping device, such as a tamping tube 212 (FIG. 5A), for advancing the sealing plug 210 along the suture 204 and toward the anchor 208. The tamping tube 212 is shown located partially within the carrier tube 202 and proximal of the sealing plug 208. The tamping tube 212, however, also extends through a handle 252 of the closure device 200. The tamping tube 212 is preferably an elongated tubular or semi-tubular rack that may be rigid or flexible and formed of any suitable material. For example, according to one embodiment, the tamping tube 212 is made of polyurethane. The suture 204 extends through at least a portion of the tamping tube 212. For example, as shown in FIGS. 5A-5G, the suture 204 extends along the tamping tube 212 between the first and second end portions 206, 207. However, the suture 204 is not directly connected to the tamping tube 212. Accordingly, the suture 204 and the tamping tube 212 may slide past one another.

According to the embodiment of FIGS. 5A-5G, the suture 204 attaches to an automatic tamping assembly. The automatic tamping assembly may include an automatic driving mechanism 630 or other transducer, and the tamping tube 212. The automatic driving mechanism 630 is located within the housing or handle 252 at the first end portion 206 of the closure device 200. Embodiments of the automatic driving mechanism 630 are described in detail below with reference to FIGS. 6-9. The tamping tube 212 may comprise a rack receptive of gear teeth (discussed in more detail below).

In practice, the carrier tube 202 of the closure device 200 (containing the closure elements described above) is inserted into the insertion sheath 216, which is already inserted within the artery 228 (FIGS. 5B-5C). As the closure device 200 and the associated closure elements are inserted into the procedure sheath 216, the anchor 208 passes through and out of the distal end of the procedure sheath 216 and is inserted into the artery lumen 232. As mentioned above and shown in FIG. 5A, the anchor 208 is initially arranged substantially flush with the carrier tube 202 to facilitate insertion of the anchor 208 through the percutaneous incision 219 and into the lumen 232.

After the anchor 208 passes out of the distal end of the procedure sheath 216, however, it tends to deploy or rotate to the position shown in FIGS. 5B-5C. The closure device 200 may also be partially withdrawn from the insertion sheath 216, catching the anchor 208 on the distal end of the insertion sheath 216 and rotating it to the position shown in FIGS. 5B-5C. However, the closure device 200 preferably includes a pair of biased fingers 215 that are lockingly received by a matching pair of recesses 217 in the procedure sheath 216. The locking arrangement between the biased fingers 215 and matching recesses 217 preferably fixes the position of the handle 252 relative to the procedure sheath 216.

Following deployment of the anchor 208, the handle 252 and the insertion sheath 216 are withdrawn together. Withdrawing the handle 252 causes the anchor 208 to anchor itself within the artery 228 against the artery wall 234. With the anchor 208 anchored within the artery 228 at the puncture site 218, further retraction of the handle 252 and insertion sheath 216 tends to pull the sealing plug 210 out from the distal end portion 207 of the carrier tube 202, thereby depositing the plug 210 within the incision or puncture tract 219. The slit 209 (FIG. 5A) in the carrier tube 202 allows the distal end portion 207 of the carrier tube to flex or open, facilitating ejection of the sealing plug 210. However, the slit 209 (FIG. 5A) at the distal end portion 207 of the carrier tube 202 may be prevented from opening or flexing by the procedure sheath 216, which is concentric with the carrier tube 202. Therefore, according to principles of the present invention, retraction of the handle 252 and insertion sheath 216 causes the insertion sheath 216 to retract with respect to the carrier tube 202 to a second position shown in FIGS. 5D-5E.

Figures 5D, 5E:
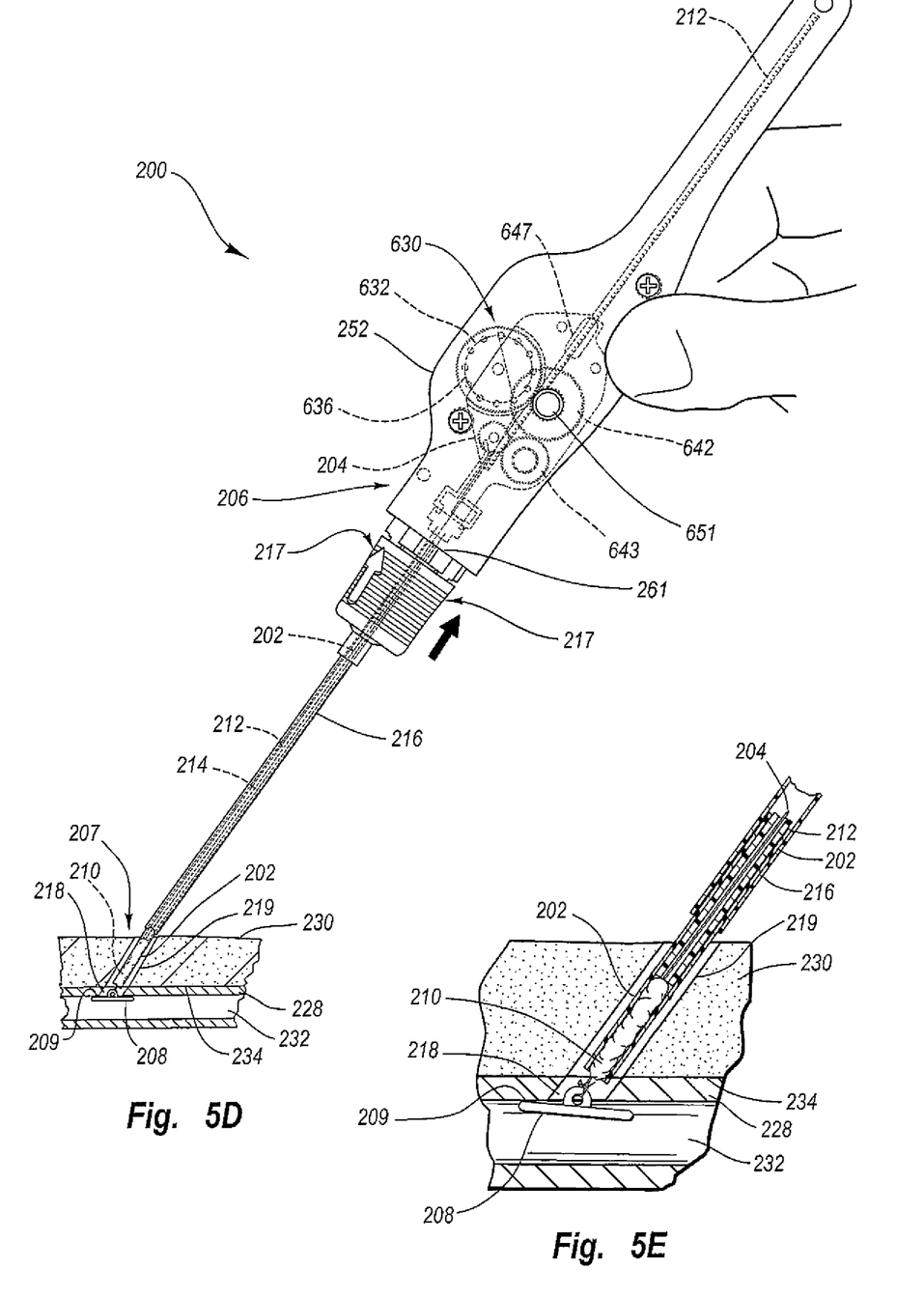
FIG. 5D is a side view of the tissue closure device of FIG. 5A shown engaged with an artery in a second position retracting the procedure sheath according to one embodiment of the present invention.
FIG. 5E is a detailed inset of FIG. 5D.

Referring to FIGS. 5D-5E, the distal end portion 207 of the carrier tube 202 is exposed (within the incision tract 219) as the handle 252 and the procedure sheath 216 are retracted. The carrier tube 202 retains its position relative to the puncture 218 until the handle 252 and the procedure sheath 216 have been retracted a predetermined distance. Relative movement between the handle 252/procedure sheath 216 and the carrier tube 202 is facilitated by a sliding mount arrangement between the automatic driving mechanism 630 and the handle 252. However, according to some embodiments the automatic driving mechanism 630 is fixed to the handle 252.

Figure 8:
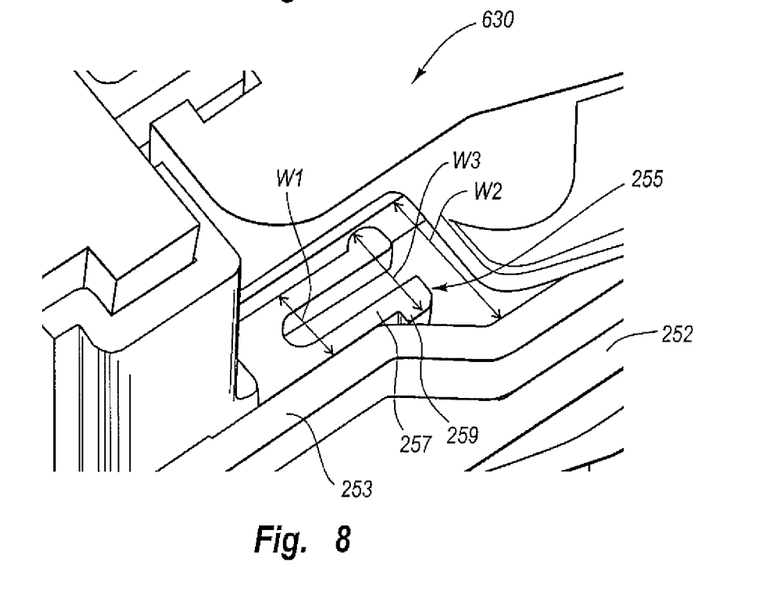
FIG. 8 is blown up perspective view of a portion of the driving mechanism and handle of FIG. 5A according to one embodiment of the present invention.

As shown by the combination of FIGS. 5B-5G, the automatic driving mechanism 630 (which is attached to the carrier tube 202) is preferably free floating or displaceable and slides relative to the handle 252 as the handle 252 and the procedure sheath 216 are retracted. However, the automatic driving mechanism 630 may be initially held in a first position relative to the handle 252 as shown in FIGS. 5B and 8. For example, as shown in FIG. 8, the automatic driving mechanism 630 may comprise a temporary holder such as a stowage detent 255 slidingly mounted in a track. The track is shown in FIG. 8 as a webbing track 253. The webbing track 253 is disposed in the handle 252. The webbing track 253 may have a first width W1 and a second width W2. The stowage detent 255 may include a finger 257 with a protrusion 259 biased to a third width W3 greater than the first width W1, but less than the second width W2. The finger 257 extends at least partially into the webbing track 253 at the second width W2 to at least temporarily hold the automatic driving mechanism 630 in the first position shown in FIGS. 5B and 8, and prevent premature sliding within the handle 252.

Although the finger 257 tends to hold or temporarily lock the automatic driving mechanism 630 in the first position shown in FIGS. 5B and 8, the finger 257 releases when a sufficient predetermined force is applied between the handle 252 and the automatic driving mechanism 630. For example, with the anchor 208 deployed, a retraction force provided by a user to the handle 252 causes the finger 257 to deflect inward and slide distally toward the first width W1 portion of the webbing track 253. When the protrusion 259 of the finger enters the first width W1, the stowage detent 255 is "released" and provides very little resistance to sliding movement between the automatic driving mechanism 630 and the handle 252. Accordingly, retraction of the handle 252 retracts the procedure sheath 216 (which is fixedly connected to the handle 252), but the automatic driving mechanism 630 and the carrier tube 202 slide relative to the handle 252 and therefore remain in position with respect to the puncture 218. The automatic driving mechanism 630 may slide a predetermined distance with respect to the handle 252 until the automatic driving mechanism 630 reaches a stop 261. The predetermined distance is preferably at least long enough to fully expose the slit 209 (FIG. 5A) in the carrier tube 202.

Figures 5F, 5G:
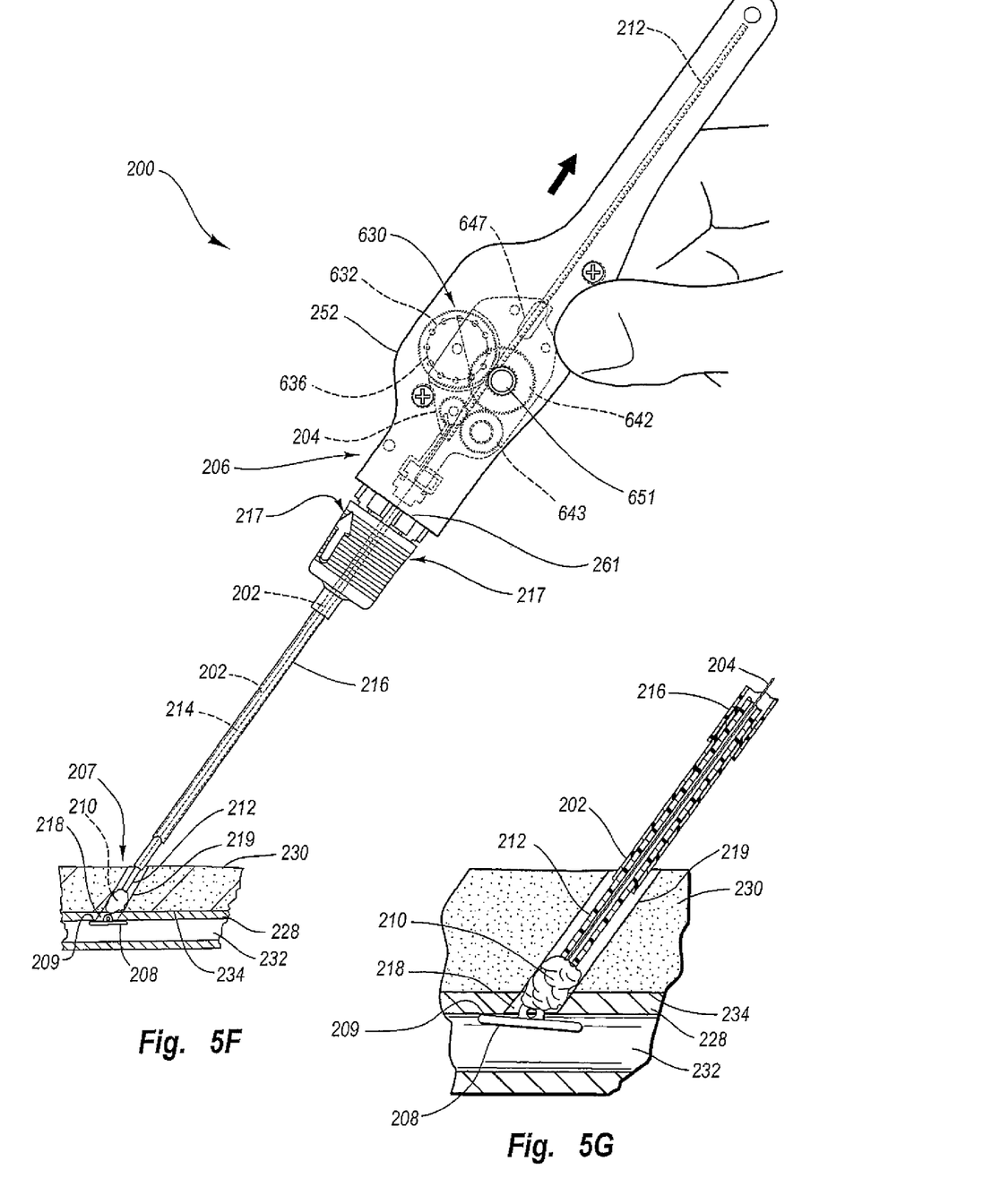
FIG. 5F is a side view of the tissue closure device of FIG. 5A shown engaged with an artery in a third position tamping a sealing plug according to one embodiment of the present invention.
FIG. 5G is a detailed inset of FIG. 5F.

When the automatic driving mechanism 630 reaches the stop 261 (FIG. 5D), further retraction of the handle 252 withdraws the carrier tube 202 as well, ejecting and tamping the sealing plug 210 automatically as shown in FIGS. 5F-5G. Unlike previous closure devices that require a separate, manual tamping procedure following the deposition of the sealing plug 210, the closure device 200 of the present invention automatically tamps the sealing plug 210. The sealing plug 210 is tamped while the carrier tube 202 is being withdrawn, reducing or eliminating any gaps that may otherwise occur between the sealing plug 210 and the puncture 218 in the femoral artery 228.

In addition, by placing tension on or pulling the suture 204 away from the puncture tract 219, the suture 204 may cinch and lock (with a slip knot or the like) together the anchor 208 and the sealing plug 210, sandwiching the artery wall 234 between the anchor 208 and sealing plug 210. The force exerted by the tamping tube 212 and the cinching together of the anchor 208 and sealing plug 210 by the filament 204 also causes the sealing plug 210 to deform radially outward within the puncture tract 219 and function as an anchor on the proximal side of the tissue puncture site 218 as shown in FIGS. 5F-5G.

The tamping tube 212 is automatically driven toward the sealing plug 210 by the automatic driving mechanism 630. One embodiment of the automatic driving mechanism 630 is shown in detail in FIG. 6. The automatic driving mechanism 630 may comprise a gearbox assembly 629, and the gearbox assembly 629 may be selectably disengagable. According to the embodiment of FIG. 6, once the automatic driving assembly 630 contacts the stop 261, further retraction of the closure device 200 automatically effects tamping of the sealing plug 210 (FIG. 5F).

Figure 6:
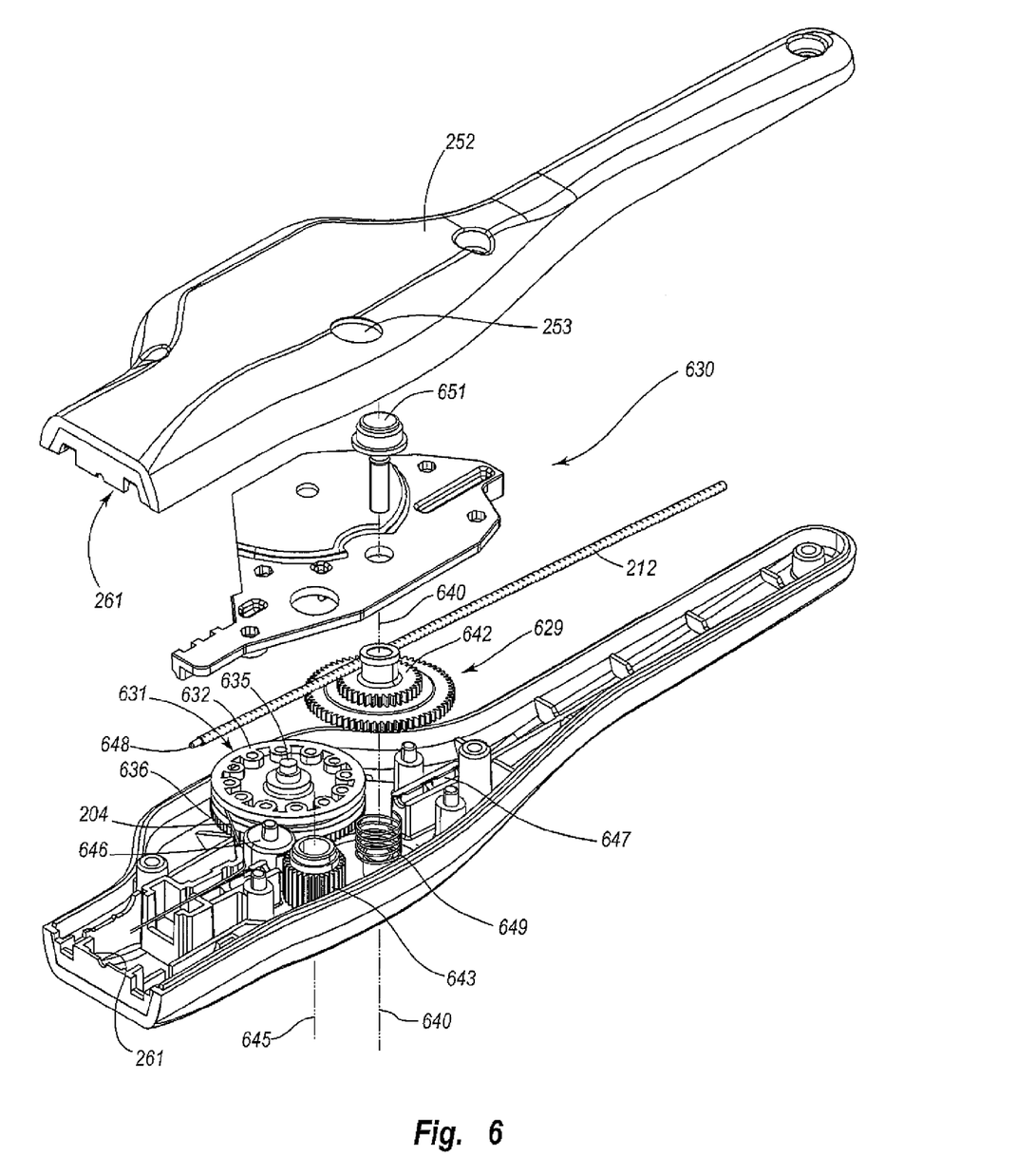
FIG. 6 is illustrates the driving mechanism of FIG. 5A in a perspective assembly view with a carrier tube removed for clarity according to one embodiment of the present invention.

According to the gearbox assembly 629 of FIG. 6, the suture 204 is connected to and partially wound about a spool 632 of a first gear an spool assembly 631. The first gear and spool assembly 631 includes both the spool 632 and a first gear 636 arranged on a first axis 635. According to the embodiment of FIG. 6, the first gear 636 is connected to the spool 632 and therefore they rotate together. Withdrawal of the closure device 200 (FIG. 5F) from the tissue puncture site 218 (if the anchor 208 (FIG. 5F) is deployed and the gearbox assembly 629 has contacted the stop 261) causes the suture 204 to unwind from the spool 632. The spool 632 rotates as the suture 204 unwinds and provides a torsional motive force that is transduced to a linear tamping force.

The torsional motive force provided by the spool 632 is transduced into the linear tamping force by the gearbox assembly 629 according to the embodiment of FIG. 6. The gearbox assembly 629 includes the first gear 636 arranged coaxially with the spool 632. As shown in FIG. 6, the first gear 636 may be arranged adjacent to a second gear 642. The second gear 642, when assembled, engages the first gear 636. The second gear 642 is arranged on a second axis 640. The second gear 642 may be a two-stage gear, with each stage engaging a different adjacent gear as shown. The first and second gears 636 and 642 may engage one another with a frictional fit, or with meshed gear teeth as shown. The second gear 642 is arranged adjacent to a third gear 643 on a third axis 645. When assembled, the second gear 642 engages and drives the third gear 643.

The tamping tube 212 is disposed between the third gear 643 and a guide 646. The tamping tube 212 preferably includes the teeth shown, which mesh with teeth of the third gear 643. A concave holder 647 may support the tamping tube 212. When the spool 632 rotates, it drives the tamping tube 212, which in turn tamps the sealing plug 210 (FIG. 5F). Alternatively, the tamping tube 212 may not extend into the housing 252, and instead a separate rack may mesh with the third gear 643. The separate rack would, in turn, drive the tamping tube 212.

The tamping tube 212 is preferably semi-tubular and partially disposed about the suture 204 along its longitudinal axis. The semi-tubular shape of the tamping tube 212 has a generally U-shaped cross section, and provides an open channel or trough 648 through which the suture 204 may enter and exit. The open channel 648 permits the suture and the tamping tube 212 to merge as the spool 632 unwinds. The suture 204 and the tamping tube 212 are not fixedly connected to one another, allowing each to slide freely past the other. Accordingly, with the anchor 208 (FIG. 5D) deployed, as the closure device 200 (FIG. 5F) is retracted in a first direction with the gearbox assembly 629 bearing against the stop 261 (FIG. 5F), the suture 204 unwinds from the spool 632, which drives the gearbox assembly 629. The gearbox assembly 629 drives the tamping tube 212 in a second, opposite direction, and the tamping tube tamps the sealing plug 210 (FIG. 5F).

It may be desirable in some cases to increase the linear velocity of the tamping tube 212 relative to the linear velocity at which the closure device 200 (FIG. 5F) is withdrawn. Increasing the linear velocity for the tamping tube 212 may better assure that the sealing plug 210 (FIG. 5F) is forced toward the anchor 208 (FIG. 5F) when the closure device 200 (FIG. 5F) is withdrawn in an opposite direction. Therefore, according to some embodiments, the gearbox assembly 629 may have an overall gear ratio greater than 1:1. For example, the gear ratio may range between approximately 1.5:1 and 3.0:1 for some embodiments, while the gear ratio is about 2.1:1 in other embodiments However, it should be noted that the linear velocity of the tamping tube 212 should not be excessively greater than the linear velocity of withdrawal of the closure device, as excessive speed could potentially force the sealing plug 210 (FIG. 5F) through the tissue puncture 218 (FIG. 5F) and into the lumen 232 (FIG. 5F) of the artery 228 (FIG. 5F). Likewise, an insufficient opposing force against the anchor 208 (FIG. 5F) could potentially result in the anchor 208 (FIG. 5F) being pulled out of place from within the artery 228 (FIG. 5F). Therefore, according to some uses, the withdrawal force should not exceed approximately 2.5 pounds.

It will be understood by those of skill in the art having the benefit of this disclosure that the gearbox assembly 629 configuration shown in FIG. 6 is exemplary in nature, and not limiting. Any gear configuration (including a single gear) may be used to transmit a motive force generated by retraction of the suture 204 from the closure device 200 (FIG. 5F) to provide an automatic driving force to the sealing plug 210 (FIG. 5F) via the tamping tube 212.

As mentioned above, the gearbox assembly 629 may be selectable disengagable. Therefore, one or more of the spool 632, first gear 636, second gear 642, and third gear 643 may be movable to disengage or manually disable adjacent gears. For example, one or more of the first gear 636, second gear 642, or third gear 643 may be movable along its respective axis to disengage from an adjacent gear. As shown in FIG. 6, a biasing member such as a spring 649 is disposed at the second axis 640 biasing the second gear 642 into a meshed relationship with the first and third gears 636, 643. However, the second gear 642 is movable along the second axis 640 by operation of an actuator 651 coupled to the second gear 642. Therefore, a force may be applied to the actuator 651 (following sliding movement of the gearbox assembly 629 to reach the stop 261, thereby aligning the actuator 651 with an access hole 253 in the handle 252) laterally along the second axis 640 (see FIG. 6) with respect to the second gear 642, the first direction of retraction of the closure device 200, and the second direction of driving the tamping tube 212 toward the sealing plug 210, to overcome a biasing force provided by the spring 649 and move or displace the second gear 642 axially out of the meshed or contacting relationship with at least one of the first and third gears 636, 643. According to the embodiment of FIG. 6, axial movement of the second gear 642 only disengages the second gear 642 from the first gear 636. Disengaging the gearbox assembly 629 allows retraction of the closure device 200 (FIG. 5F) and unwinding of the suture 204 from the spool 632 without driving the tamping tube 212. The advantages of this disengagement are discussed below with reference to the operation of the closure device 200.

Figure 7:
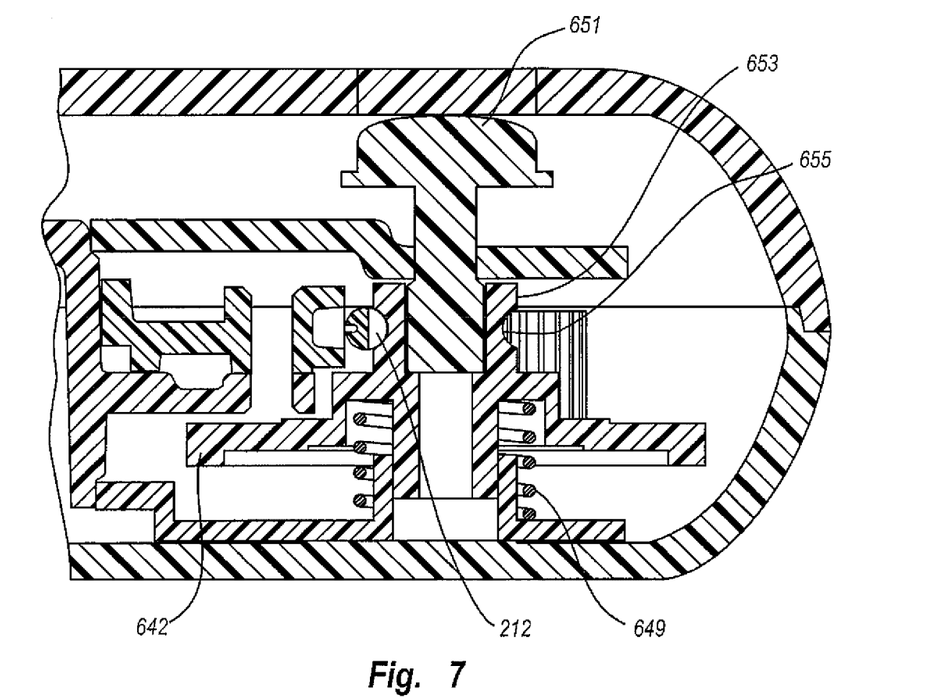
FIG. 7 is a side cross sectional view of the driving mechanism of FIG. 6 according to one embodiment of the present invention.

However, as shown in FIGS. 6-7, the tamping tube 212 may interlock with the second gear 642 in a first rack position shown, preventing premature activation of the actuator 651. The interlocking geometry is seen more clearly in FIG. 7. The second gear 642 may include a second gear hub 653 with an annular groove 655. The tamping tube 212 is disposed in the annular groove 655 in the first rack position, which locks out the actuator 651. The tamping tube rests on the concave holder 647. Therefore, as long as the tamping tube 212 is disposed in the annular groove 655, the actuator 651 may not be depressed. With the tamping tube 212 disposed in the annular groove 655, forces applied to the actuator 651 are transmitted to the second gear 642, but the second gear is prevented from moving axially by the rack disposed in the annular groove 655 and supported by the concave holder 647. Nevertheless, retracting the closure device 200 (FIG. 5F) results in rotation of the gears of the gearbox assembly 629, and linear movement of the tamping tube 212. When the tamping tube 212 has moved a predetermined distance to a second tamping tube position sufficient to cause effective tamping of the sealing plug 210 (FIG. 5F), the tamping tube 212 also moves out of the annular groove 655 (See FIG. 5F). Therefore, the actuator 651 is no longer locked out, and the second gear 642 may be disengaged once the tamping tube 212 has moved linearly the predetermined distance.

Operation of the embodiment of FIGS. 5A-8 is as follows. As the handle 252 of the closing device 200 is retracted from the puncture tract 219 as shown in FIG. 5B, the detent 255 releases. The automatic tamping mechanism 630 and carrier tube 202 remain stationary and therefore float relative to the handle 252. The procedure sheath 216 is retracted as the handle 252 is withdrawn, exposing the distal end 207 of the carrier tube 202. The automatic tamping mechanism 630 eventually contacts a stop 261, and further retraction causes the automatic tamping mechanism 630 and carrier tube 202 to retract as well. As the automatic tamping mechanism 630 retracts, the suture 204, which is threaded through the anchor 208, unwinds from and causes rotation of the spool 632. The spool 632 drives the first gear 636 as it rotates via the coaxial connection between the spool 632 and the first gear 636. As the first gear 636 rotates, it drives the second gear 642. The second gear 642 drives the third gear 643, and the third gear 643 drives the tamping tube 212. The tamping tube 212 tamps the sealing plug 210. Therefore, as the closing device 200 is retracted from the puncture tract 219, the procedure sheath 216 is retracted (FIGS. 5D-5E), and the sealing plug 210 is automatically tamped (FIGS. 5F-5G). The sealing plug 210 is more likely to create a sufficient arterial seal without a gap relative to the anchor 208, as may otherwise occur with a separate manual tamping procedure.

Moreover, when the sealing plug 210 has been sufficiently tamped, the selectably disengagable gearbox assembly 629 may be disengaged, enabling further retraction of the closure device 200 without additional tamping. With the sealing plug 210 fully tamped, there may be little or no portion of the suture 204 extending outside of the tissue layer 230 and exposed to an operator. Therefore, it may be difficult for an operator to separate the sealing plug 210 and anchor 208 from the remainder of the closure device 200. In addition, too much retraction with the selectably disengagable gearbox assembly 629 enabled could potentially overtamp the sealing plug 210 into the artery 228. Accordingly, the selectably disengagable gearbox assembly 629 may be advantageously disabled by activating the actuator 651 through the access hole 253. Activating the actuator 651 allows the suture 204 to fully unwind from the spool 632 without driving the tamping tube 212. Unwinding the spool 632 exposes a sufficient length of the suture 204 to allow an operator to easily cut it and separate the sealing plug 210 and anchor 208 from the remainder of the closure device 200.

Figure 9:
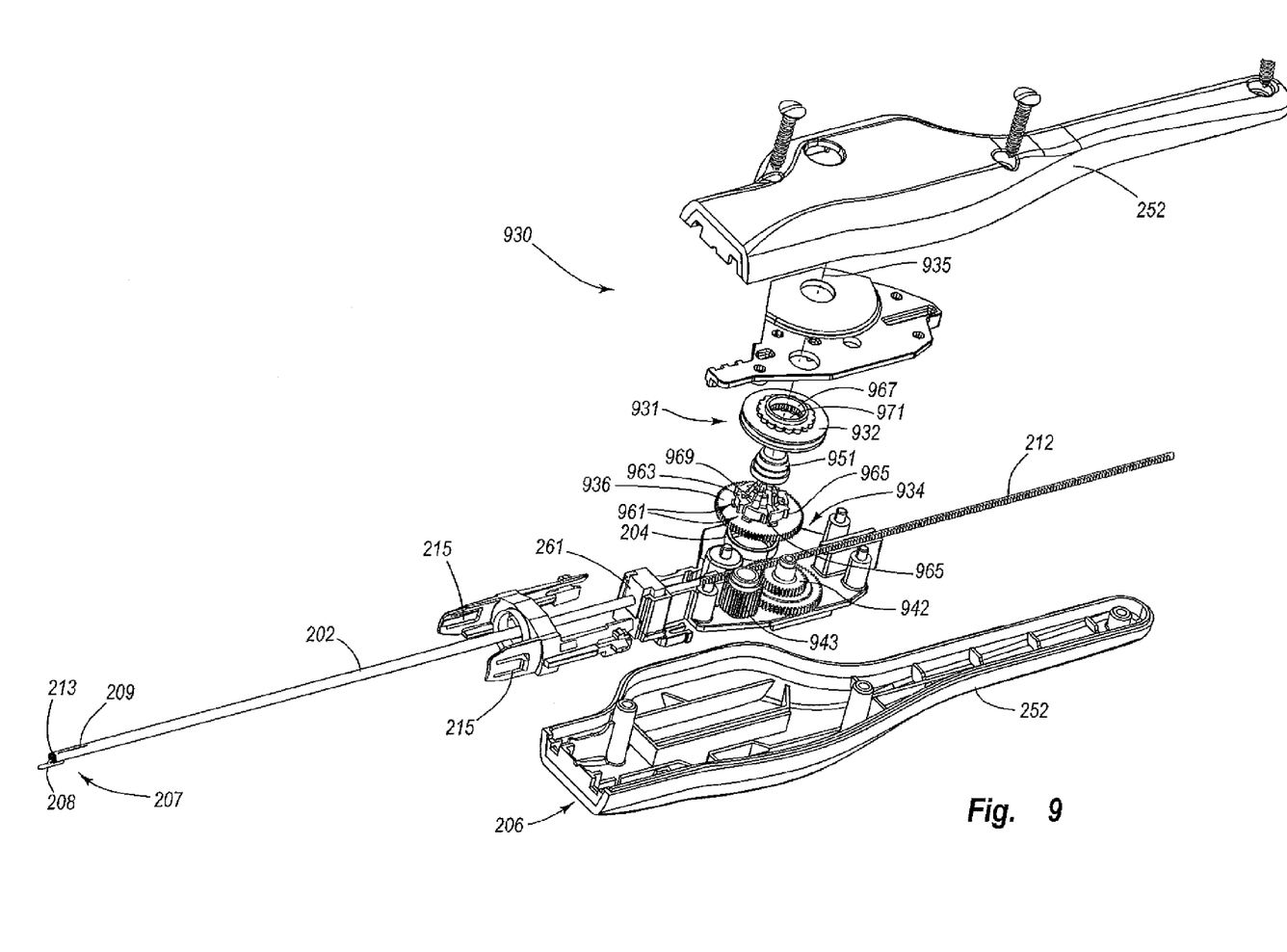
FIG. 9 is a perspective assembly view of a tissue puncture closure device with an automatic tamping or driving mechanism according to another embodiment of the present invention.

Referring next to FIG. 9, another embodiment of a selectably disengagable automatic driving mechanism 930 is shown. The selectably disengagable automatic driving mechanism 930 of FIG. 9 may replace the selectably disengagable gearbox assembly 629 shown in FIG. 6 within the closure device 200 (FIG. 5A). Similar to the embodiment of FIG. 6, the selectably disengagable automatic driving mechanism 930 of FIG. 9 includes the suture 204 at least partially wound about a spool 932 of a first gear and spool assembly 931. The first gear and spool assembly 931 includes both the spool 932 and a first gear 936 arranged on a first axis 935. However, according to the embodiment of FIG. 9, the first gear 936 and the spool 932 form a manually operated clutch therebetween. The clutch may be used to selectively connect and disconnect the first gear 936 from the spool 932. The clutch comprises a plurality of release fingers 961 in FIG. 9. The release fingers 961 are arranged substantially in a circle. A first component 963 of the release fingers 961 is cantilevered from the first, gear 936 and extends normal to the first gear 936. A protrusion 965 of the first component 963 extends radially outward and is received by a mating recess 967 of the spool 932. A second component 969 of the release fingers 961 arcs substantially normal to the first component 963 and the first gear 936. The second component 969 of each of the release fingers 961 extends through a central hole 971 of the spool 932. An actuator button 951 fits over and contacts the second components 969 of each of the release fingers 961.

The fit of the protrusions 965 of the first gear 936 with the mating recesses 967 of the spool 932 causes the first gear 936 and spool 932 to rotate together at an identical angular velocity. However, when the actuator button 951 is depressed, the actuator button slides along the arcs of the second component 969, forcing each of the release fingers 961 radially inward. The radial inward displacement of the release fingers 961 at least partially removes the protrusions 965 from the mating recesses 967, allowing independent rotation of the spool 932 with respect to the first gear 936. Therefore, similar to the arrangement described above with reference to FIGS. 5A-8, after the seating plug 210 is driven toward the anchor 208, the selectably disengagable automatic driving mechanism 930 is disengaged or disabled, allowing the suture 204 to safely unwind without further tamping. The suture 204 is then exposed to the operator for convenient cutting.

The remaining components of the selectably disengagable automatic driving mechanism 930 may be similar to the embodiment of FIG. 6. Transducing the torsional motive force provided by the spool 932 to the linear tamping force is achieved by a gear train 934. The gear train 934 may include the first gear 936 and second and third gears 942, 943. As shown, the second gear 942 engages and drives the third gear 943, and the third gear 943 drives a tamping tube 212 or other sealing plug driving device. The second gear 942 of FIG. 9 does not, however, include an annular groove interlocking with the tamping tube 212.

The preceding description has been presented only to illustrate and describe exemplary embodiments of invention. It is not intended to be exhaustive or to limit the invention to any precise form disclosed. Many modifications and variations are possible in light of the above teaching. It is intended that the scope of the invention be defined by the following claims.

What is claimed is:

1. A method of sealing a tissue puncture in an internal tissue wall accessible through a percutaneous incision, comprising:
   withdrawing a closure device from the tissue puncture;
   automatically transducing a motive force generated by withdrawal of the closure device in a first direction to a cinching or tamping force in a second direction;
   disabling the tamping force in the second direction by manually operating an actuator laterally with respect to at least one of the first and second directions.

2. A method of sealing a tissue puncture in an internal tissue wall accessible through a percutaneous incision according to claim 1, further comprising applying the cinching or tamping force in the second direction to a sealing plug.

3. A method of sealing a tissue puncture in an internal tissue wall accessible through a percutaneous incision according to claim 2, further comprising transferring the motive force to a rack that is slidingly disposed about a filament, the filament being connected to the sealing plug.

4. A method of sealing a tissue puncture in an internal tissue wall accessible through a percutaneous incision according to claim 3 wherein the transferring further comprises automatically unwinding the filament from a spool by deploying an anchor attached to the filament inside the tissue puncture, and withdrawing the closure device from the tissue puncture.

5. A method of sealing a tissue puncture in an internal tissue wall accessible through a percutaneous incision according to claim 4 wherein the transferring further comprises driving a gear train meshed with the rack and the spool via the unwinding.

6. A method of sealing a tissue puncture in an internal tissue wall accessible through a percutaneous incision according to claim 5, further comprising driving a tamping device with the rack to provide the tamping force to the sealing plug.

7. A method of sealing a tissue puncture in an internal tissue wall accessible through a percutaneous incision according to claim 5, wherein the manually disabling the tamping force in the second direction comprises disengaging at least one gear of the gear train.

8. A method of sealing a tissue puncture in an internal tissue wall accessible through a percutaneous incision according to claim 7, wherein the disengaging comprises axially displacing at least one gear out of contact with an adjacent gear.

9. A method of sealing a tissue puncture in an internal tissue wall accessible through a percutaneous incision according to claim 8 wherein the axially displacing comprises applying a force to an external actuator operatively connected to the at least one gear against an opposing biasing force.

10. A method of sealing a tissue puncture in an internal tissue wall accessible through a percutaneous incision according to claim 8, further comprising:
  releasing the rack from an interlock with the at least one gear prior to axially displacing the at least one gear.

11. A method of sealing a tissue puncture in an internal tissue wall accessible through a percutaneous incision according to claim 5, wherein the disabling comprises disconnecting the spool from the gear train.

12. A method of sealing a tissue puncture in an internal tissue wall accessible through a percutaneous incision, comprising:
  providing a tissue puncture closure device comprising a filament connected at its distal end to an anchor and to a sealing plug located proximal of the anchor for disposition and anchoring about the tissue puncture, the tissue puncture closure device also comprising an automatic tamping device;
  inserting the tissue puncture closure device into the percutaneous incision;
  deploying the anchor into the tissue puncture;
  at least partially withdrawing the closure device from the percutaneous incision;
  automatically tamping the sealing plug toward the anchor upon withdrawal of the closure device from the internal tissue wall puncture with the automatic tamping device;
  disengaging the automatic tamping device by operating an actuator laterally with respect to a direction of tamping the sealing plug toward the anchor;
  retracting the tissue puncture closure device;
  exposing the filament;
  cutting the filament;
  leaving the anchor and the sealing plug at the tissue puncture.

13. A method of sealing a tissue puncture in an internal tissue wall accessible through a percutaneous incision, comprising:
  withdrawing a closure device from the tissue puncture;
  automatically transducing a motive force generated by withdrawal of the closure device in a first direction to a cinching or tamping force in a second direction;
  manually disabling the tamping force in the second direction;
  wherein the manually disabling the tamping force in the second direction comprises disengaging at least one gear of a gear train.

14. A method of sealing a tissue puncture in an internal tissue wall accessible through a percutaneous incision according to claim 13, wherein the disengaging comprises axially displacing at least one gear out of contact with an adjacent gear.

15. A method of sealing a tissue puncture in an internal tissue wall accessible through a percutaneous incision according to claim 14 wherein the axially displacing comprises applying a force to an external actuator operatively connected to the at least one gear against an opposing biasing force.

16. A method of sealing a tissue puncture in an internal tissue wall accessible through a percutaneous incision according to claim 14, further comprising:
  releasing the rack from an interlock with the at least one gear prior to axially displacing the at least one gear.

* * * * *